US006944897B2

(12) United States Patent
Koch

(10) Patent No.: US 6,944,897 B2
(45) Date of Patent: Sep. 20, 2005

(54) ARRANGEMENT FOR HOLDING ACCESSORY PARTS TO A PATIENT SUPPORT SURFACE

(75) Inventor: Guido Koch, Karlsruhe (DE)

(73) Assignee: Maquet GmbH & Co. KG, Rastatt (DE)

( * ) Notice: Subject to any disclaimer, the term of this patent is extended or adjusted under 35 U.S.C. 154(b) by 75 days.

(21) Appl. No.: 10/415,776

(22) PCT Filed: Nov. 16, 2001

(86) PCT No.: PCT/EP01/13283

§ 371 (c)(1), (2), (4) Date: May 1, 2003

(87) PCT Pub. No.: WO02/41822

PCT Pub. Date: May 30, 2002

(65) Prior Publication Data

US 2004/0088793 A1 May 13, 2004

(30) Foreign Application Priority Data

Nov. 21, 2000 (DE) .................................... 200 19 728 U

(51) Int. Cl.$^{7}$ .......................... A61G 13/10; A61B 6/00; B25B 5/00

(52) U.S. Cl. ................................ 5/621; 5/601; 5/503.1; 5/658; 378/208; 378/209; 248/316.1

(58) Field of Search ............................ 5/612–624, 600, 5/601, 658, 503.1; 248/689, 229.1, 229.13–229.16, 229.23–229.26, 226.11, 316.1, 228.4–228.7, 230.4–230.7, 231.51–231.81, 316.5–316.7; 24/455, 457, 445; 108/27, 28, 65, 90; 378/177, 195, 208, 209

(56) References Cited

U.S. PATENT DOCUMENTS 1,797,847 A 3/1931 Vandagriff et al.
3,967,126 A * 6/1976 Otto, Jr. ..................... 378/177
4,146,793 A * 3/1979 Bergstrom et al. .......... 378/161
4,484,571 A * 11/1984 Velazquez ....................... 5/601
4,583,242 A * 4/1986 Vinegar et al. ............... 378/20
4,698,837 A * 10/1987 Van Steenburg ............ 378/208
4,796,846 A * 1/1989 Meier et al. ............. 248/286.1
4,898,491 A * 2/1990 Van Steenburg ............. 403/96
5,077,780 A * 12/1991 Lee, Jr. ...................... 378/196
5,156,166 A 10/1992 Sebring ...................... 128/845
5,174,533 A * 12/1992 Pryor et al. ............ 248/288.51
5,230,112 A 7/1993 Harrawood et al. ........... 5/607
5,287,575 A 2/1994 Allen et al. ..................... 5/623
5,326,059 A * 7/1994 Pryor et al. ............ 248/231.71
5,385,324 A * 1/1995 Pryor et al. .............. 248/228.3
6,022,143 A * 2/2000 Helmreich .................. 378/181
6,023,800 A 2/2000 Stickley .......................... 5/621
6,027,247 A * 2/2000 Tachi et al. ................. 378/196
6,315,260 B1 * 11/2001 Lees ......................... 28/286.1
6,499,158 B1 * 12/2002 Easterling ...................... 5/600

(Continued)

FOREIGN PATENT DOCUMENTS

DE 200 16 235 U1 1/2001

OTHER PUBLICATIONS

Copy of International Search Report for PCT/EP01/13283 dated Mar. 22, 2002.

*Primary Examiner*—Robert G. Santos
(74) *Attorney, Agent, or Firm*—McCormick, Paulding & Huber LLP

(57) ABSTRACT

The invention relates to a system for supporting accessories on a patent resting surface of an operation or examination table (10) comprising an accessory adapter (24) that can be slipped on the profile of the patient resting surface (14). Support elements (32) for accessories are fastened to said accessory adapter. The adapter (14) comprises two claws (26) adapted to encompass the longitudinal edges of the patient resting surface. Said claws are interlinked via a bracket (28) that extends across a width of the patient resting surface.

12 Claims, 2 Drawing Sheets

U.S. PATENT DOCUMENTS

| | | | | | |
|---|---|---|---|---|---|
| 6,598,275 | B1 | * | 7/2003 | Kolody et al. | 24/455 |
| 6,622,980 | B2 | * | 9/2003 | Boucher et al. | 248/231.51 |
| 6,671,904 | B2 | * | 1/2004 | Easterling | 5/601 |
| 2003/0061660 | A1 | * | 4/2003 | Easterling | 5/600 |
| 2003/0155478 | A1 | * | 8/2003 | Easterling | 248/316.1 |
| 2003/0205176 | A1 | * | 11/2003 | Kolody et al. | 108/28 |
| 2004/0088793 | A1 | * | 5/2004 | Koch | 5/621 |
| 2004/0216232 | A1 | * | 11/2004 | Bradcovich | 5/601 |

* cited by examiner

ARRANGEMENT FOR HOLDING ACCESSORY PARTS TO A PATIENT SUPPORT SURFACE

Applicants hereby claim foreign priority benefits under 35 U.S.C. § 119 of PCT Patent Application No. PCT/EP01/13283 filed Nov. 16, 2001 and German Patent Application No. 200 19 728.2 filed Nov. 21, 2000, the disclosures of which are herein incorporated by reference.

BACKGROUND OF THE INVENTION

1. Technical Field

The invention concerns an arrangement for holding accessory parts to a patient support surface of an operating table or examination table.

2. Background Information

Customary operating tables have slide rails along the longitudinal edges of the involved operating table surface or patient support surface, onto which slide rails different accessory parts can be mounted with the help of clamping dogs. Such accessory parts are, for example, supports for arm rests, anesthetic bows for the holding of anesthetic equipment, body straps, and so forth.

Special medical examinations and surgical procedures require the use of X-ray devices and therefore make necessary patient support surfaces which have artifact-free transmissibility. Metal slide rails of the aforementioned type accordingly disturb the transmissibility of the support surfaces. For these reasons support surfaces have been developed which consist entirely of X-ray transmitting material, for example, carbon fiber reinforced plastic. But with this the problem exists in that the accessory parts can no longer be fastened in the usual way to the patient support surface itself; and for example are held on their own stands. This once again hinders access to the patient support surface.

BRIEF SUMMARY OF THE INVENTION

The invention has as its object the provision of an arrangement of the previously mentioned kind for the holding of accessory parts which makes possible the mounting of accessory parts also to patient support surfaces which are made of X-ray transmitting material.

This object is solved in accordance with the invention by an accessory adapter mountable onto the profile of the patient support surface and onto which adapter holding elements for accessory parts are fastened.

The solution according to the invention has the feature that the accessory adapter can be shifted along the patient support surface or if need be entirely removed from it, in order to not interfere with the transmission of X-rays through the patient support surface. On the other hand, the accessory parts can still be directly mounted onto the patient support surface so that they assure free access to the patient support surface.

In a preferred embodiment the adapter has two jaws which receive the longitudinal edges of the patient support surface, which jaws are connected with one another by a bow extending across the width of the patient support surface. This bow can be made of one piece with the jaws, and as to its shape can be suited to the profile of the patient support surface so that it requires little space. The accessory adapter further, entirely or at least in the region of the bow, can be made of an X-ray transmitting material, such as for example carbon fiber reinforced plastic, so that it need not be removed or shifted for all X-ray examinations.

Preferably, fastening means are provided on the accessory adapter to fix it in a desired position relative to the patient support surface and to prevent an inadvertent shifting of the accessory relative to the patient. Advantageously the fastening means are arranged on at least one of the jaws where they can be easily operated. To be able to fix the accessory adapter to the patient support surface at a desired location, the fastening means advantageously include a clamping mechanism received in a jaw opening which makes possible a force-wise fixing of the accessory adapter. The clamping mechanism in a preferred embodiment of the invention has a clamping rail designed to lie against one edge strip of the patient support surface, which clamping rail is movably supported in the jaw opening and by a tightening element is pressable against the edge strip of the patient support surface. The clamping rail forms a clamping element of relatively large surface area by means of which the specific pressure pressing on the surface of the patient support surface by the clamping mechanism is lowered, and thereby damage to the patient support surface by the clamping mechanism is inhibited.

Further features and advantages of the invention will be apparent from the following description which in connection with the accompanying drawings explain the invention by way of an exemplary embodiment.

DETAILED DESCRIPTION OF THE INVENTION

Figure 1:
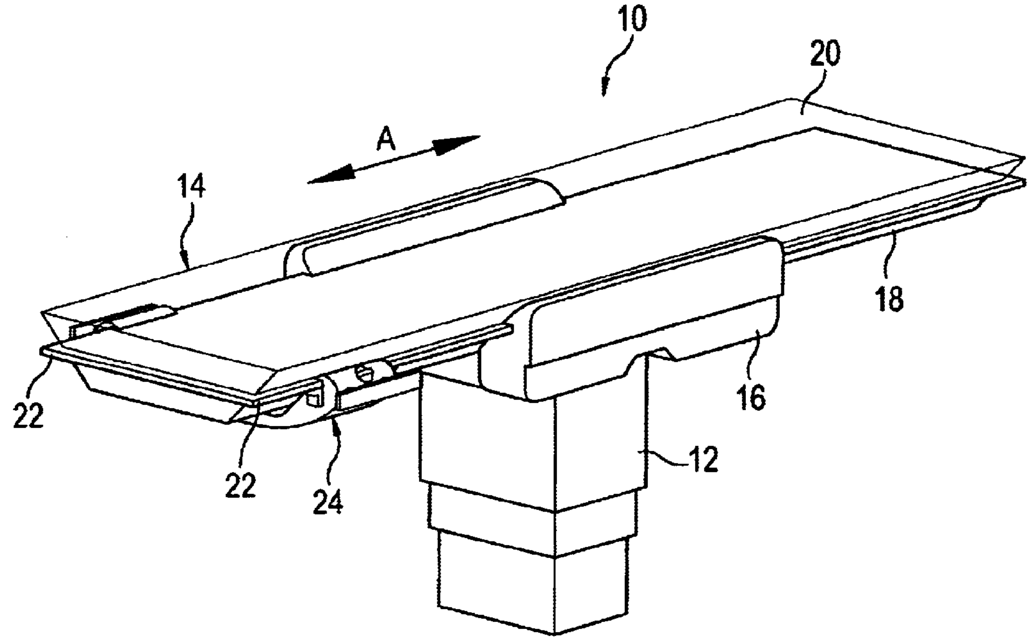
FIG. 1 a schematic perspective illustration of an operating table with a patient support surface onto which an accessory adapter according to the invention has been mounted, FIG. 2 a perspective plan view of an accessory adapter by itself, FIG. 3 a longitudinal section taken through the accessory adapter along the line III—III of FIG. 2, and FIG. 4 a cross-section through one jaw of the accessory adapter taken along the line IV—IV of FIG. 3.
Figure 2:
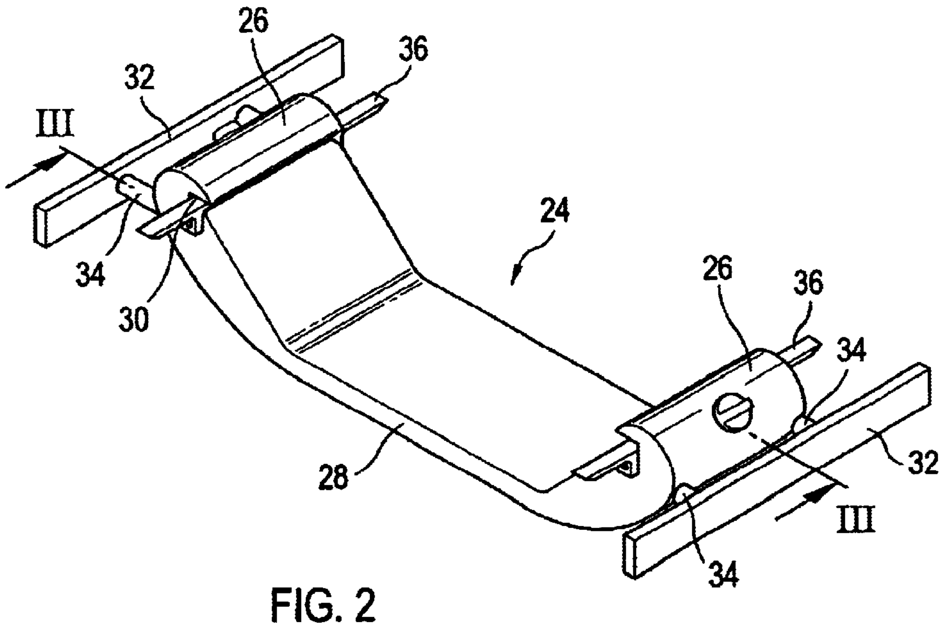
Figure 3:
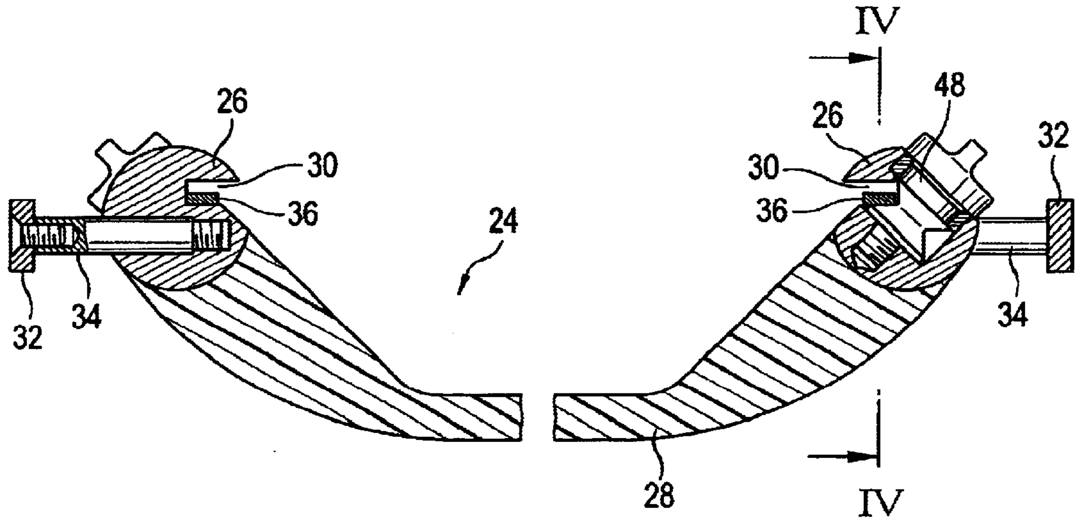

FIG. 1 shows an operating table or examination table, indicated generally at 10, with a table column 12 and a patient support surface, indicated generally at 14, which is slidably supported for movement in the direction of the double arrow A of FIG. 1, that is in its longitudinal direction, in a guide housing 16 arranged on the head of the table column 12. The patient support surface includes a table plate 18, on which a cushion 20 is arranged. The table plate 18 is made up of X-ray transmitting material, for example carbon fiber reinforced plastic, and has a trapezoidal profile which diminishes downwardly, and the trapezoid surface of which that forms the upper side of the table plate 18 is lengthened outwardly by edge strips 22 forming the edges of the table plate 18. Onto the profile of the table plate 18 is mounted an accessory adapter, indicated generally at 24, which will now be explained in more detail in connection with FIGS. 2 to 4.

The accessory adapter 24 is comprised of two jaws 26 connected with one another by a bow 28, with the jaws 26 and the bow 28 being made as one piece. Each of the claws 26 has a claw opening 30 which upon the mounting of the accessory adapter onto the table plate 18 receives a respective one of the edge strips 22. The shape of the bow 28 is suited to the trapezoidal profile of the table plate 18 so that the bow runs close to the underside of the table plate 18, when the accessory adapter 24 is pushed or mounted onto the table plate 18, as shown in FIG. 1. A slide rail 32 is fastened with the help of bolts 34 to the outer side of each jaw 26. The slide rails 32 are made of metal and have the same shape as the customary slide rails on operating table plates so that the customary accessory parts with the customary clamping mechanisms can be put onto the slide rails 32.

The fixing of the accessory adapter 24 in a desired position to the table plate 18 is accomplished with the help of clamping devices arranged in the jaws 26. Each clamping device includes a clamp rail 36 which extends in the associated jaw opening 30 parallel to the slide rail 32 and is designed to lie against the underside of one edge strip 22 of the table plate 18. The clamp rails 36 each have two downwardly directed protrusions 38 with bores 40 into each of which a bolt 42 can be screwed which in turn is receivable in a recess 44 in the accessory adapter 24. Each recess 44 perpendicular to the clamping surface 46 of the clamp rail 36 is larger than the diameter of the bolt 42 so that the clamp rail 36 can move perpendicularly to its clamping surface 46. By means of an eccentric clamping screw or toggle screw 48 threaded into the material of the associated jaw 26 the clamp rail 36 can be lifted, that is its clamping surface 46 can be tightened against the underside of the associated edge strip 22 of the table plate 18 or can be lowered. Accordingly, the accessory adapter 24 can be fixed to the table plate 18 or again loosened. As will be understood the axis of the clamping or thumb screw 48 can be inclined at an angle of about 45° with respect to the plane of the middle portion of the bow so that the clamping screw 48 can be operated comfortably and without hindrance by the slide rail 32.

If the patient support surface 14 is pushed in the guide housing 16 to X-ray certain parts of the patient, the accessory adapter 24 can either be entirely removed from the patient support surface 14 or else can be pushed to the guide housing 16 where it does not interfere with the X-ray examination. It will be understood that in the case of an operating table according to FIG. 1, for example, two such accessory adapters can be provided with, for example, each being located on a respective one of the sides of the guide housing 16.

Figure 4:
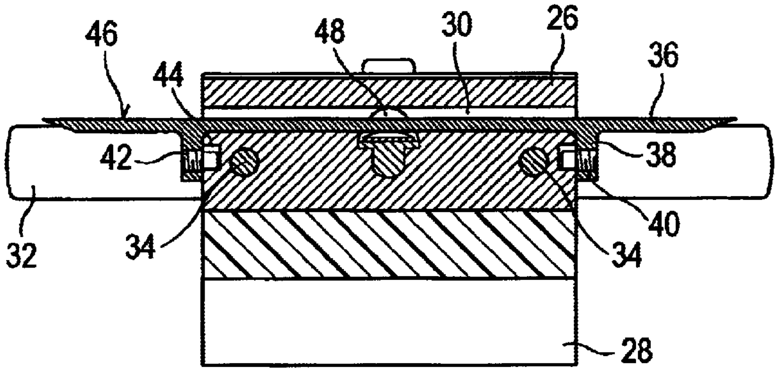

In FIG. 4 one sees that the clamp rails 36 extend outwardly from both sides beyond the jaws 26 of the accessory adapter 28. These protruding sections of the clamp rails 36 can be used as switching strips which upon the accessory adapter 24 coming close to the guide housing 16 operate a non-illustrated limit switch to turn off the drive for the movement of the support surface 14, to thereby avoid a possible collision between the guide housing and the accessory adapter 24.

It will be understood that in the case of the accessory adapter according to the invention, moments exerted about the longitudinal axis of the slide rails produced by heavy accessory parts are taken up on the opposite sides of the adapter because of the bridge-shaped connection of the two jaws of the accessory adapter. Thereby the local loading of the support surface profile is distributed over large surface areas and is reduced. The shape-wise connection of the accessory adapter with the support surface inhibits an unintended loosening of the accessory so that injury to the patient by a falling accessory can be avoided.

What is claimed is:

1. An arrangement for holding accessory parts to a patient support of an operating table or examination table the patient support having a patient support surface and a lower surface opposite the patient support surface, the arrangement comprising: an accessory adapter mountable onto a profile of the patient support to which accessory adapter are fastened holding elements for accessory parts, characterized in that the adapter has two jaws designed to receive the longitudinal edges of the patient support and to support the weight of the accessory adapter, which jaws are connected with one another by a bow extending across the width of the patient support below the lower surface, and in that the accessory adapter at least in the area of the bow is made of an X-ray transmitting material.

2. An arrangement according to claim 1, further characterized in that the bow has a shape suiting the profile of the lower surface of the patient support.

3. An arrangement according to claim 1, further characterized in that the bow is made of one piece with the jaws.

4. An arrangement according to claim 1, further characterized in that the X-ray transmitting material is carbon fiber reinforced plastic.

5. An arrangement according to claim 1, further characterized in that the holding elements are formed as slide rails of metal which are fastened to outer sides of the jaws.

6. An arrangement according to claim 1, further characterized in that fastening means are provided on the accessory adapter for fixing it to the patient support.

7. An arrangement according to claim 6, further characterized in that the fastening means are arranged on at least one of the jaws.

8. An arrangement according to claim 7, further characterized in that the fastening means include a clamping mechanism received in a jaw opening.

9. An arrangement according to claim 8, further characterized in that the clamping mechanism includes a clamp rail designed to lie against one edge of the patient support, which clamp rail is movably supported in the jaw opening and is pressable against the edge by a tightening element.

10. An arrangement according to claim 1, further characterized in that a switch operating element is provided on the accessory adapter for actuating a limit switch arranged on the patient support for switching a support drive.

11. An arrangement for holding accessory parts to a table having a patient support, the arrangement having an accessory adapter mountable onto a profile of the patient support, to which accessory adapter are fastened holding elements for accessory parts, characterized in that the adapter has two jaws designed to receive the longitudinal edges of the patient support, which jaws are connected with one another by a bow extending across the width of the patient support, and in that the accessory adapter at least in the area of the bow is made of an X-ray transmitting material, and further characterized in that the holding elements are formed as slide rails of metal which are fastened to outer sides of the jaws.

12. An arrangement for holding accessory parts to a table having a patient support, the patient support having a patient support surface, the arrangement having an accessory adapter mountable onto a profile of the patient support, to which accessory adapter are fastened holding elements for accessory parts, characterized in that the adapter has two jaws designed to receive the longitudinal edges of the patient support, which jaws are connected with one another by a bow extending across the width of the patient support, and in that the accessory adapter at least in the area of the bow is made of an X-ray transmitting material, and further characterized in that no part of the arrangement extends across the width of the patient support above the patient support surface.

* * * * *